United States Patent
Hodges et al.

(10) Patent No.: US 8,192,599 B2
(45) Date of Patent: Jun. 5, 2012

(54) METHOD AND APPARATUS FOR ELECTROCHEMICAL ANALYSIS

(75) Inventors: Alastair Hodges, Blackburn South (AU); Jerry T. Pugh, Santa Rosa, CA (US); Garry Chambers, Vermont (AU)

(73) Assignee: Universal Biosensors Pty Ltd, Rowville (AU)

( * ) Notice: Subject to any disclaimer, the term of this patent is extended or adjusted under 35 U.S.C. 154(b) by 898 days.

(21) Appl. No.: 11/284,136

(22) Filed: Nov. 21, 2005

(65) Prior Publication Data
US 2007/0205103 A1    Sep. 6, 2007

Related U.S. Application Data

(63) Continuation-in-part of application No. 11/138,080, filed on May 25, 2005.

(51) Int. Cl.
*G01N 27/327*    (2006.01)
(52) U.S. Cl. .................. 204/403.01; 204/400; 205/777.5
(58) Field of Classification Search ............ 204/403.01–403.03, 400; 205/775, 777.5, 792
See application file for complete search history.

(56) References Cited

U.S. PATENT DOCUMENTS

| | | | |
|---|---|---|---|
| 4,088,448 A | 5/1978 | Lilja et al. | |
| 4,426,451 A | 1/1984 | Columbus | |
| 4,554,064 A | 11/1985 | McClintock et al. | |
| 4,927,502 A * | 5/1990 | Reading et al. | 205/777.5 |
| 5,108,564 A | 4/1992 | Szuminsky et al. | |
| 5,120,420 A | 6/1992 | Nankai et al. | |
| 5,171,689 A | 12/1992 | Kawaguri et al. | |
| 5,312,590 A | 5/1994 | Gunasingham | |
| 5,395,504 A | 3/1995 | Saurer et al. | |
| 5,399,256 A | 3/1995 | Bohs et al. | |
| 5,437,999 A * | 8/1995 | Diebold et al. | 204/403.11 |
| 5,525,297 A | 6/1996 | Dinger et al. | |
| 5,609,823 A | 3/1997 | Harttig et al. | |
| 5,679,311 A | 10/1997 | Harttig et al. | |
| 5,741,634 A * | 4/1998 | Nozoe et al. | 204/403.03 |
| 5,797,693 A | 8/1998 | Jaeger | |
| 5,904,898 A | 5/1999 | Markart | |
| 5,942,102 A | 8/1999 | Hodges et al. | |
| 6,027,689 A | 2/2000 | Markart | |
| 6,180,063 B1 | 1/2001 | Markart | |
| 6,193,873 B1 | 2/2001 | Ohara et al. | |
| 6,251,260 B1 | 6/2001 | Heller et al. | |

(Continued)

FOREIGN PATENT DOCUMENTS

AU    54873/94    8/1994

(Continued)

OTHER PUBLICATIONS

European Search Report, Application No. EP 03 00 7604, dated May 19, 2003, 3 pages.

(Continued)

*Primary Examiner* — Alex Noguerola
*Assistant Examiner* — Gurpreet Kaur
(74) *Attorney, Agent, or Firm* — Davis Wright Tremaine, LLP

(57) ABSTRACT

Electrochemical sensors for investigating a physiological sample and methods of manufacture are disclosed. The sensor includes an electrochemical reaction cell, having electrodes and a reagent, and laterally spaced electrical contact points for electrically communication with a meter. Further described herein is a multi-chambered sensor having an electrochemical reaction cell and an immunological cell. The multi-chambered cell can also include a pre-chamber.

19 Claims, 13 Drawing Sheets

U.S. PATENT DOCUMENTS

| | | | |
|---|---|---|---|
| 6,284,125 B1 | 9/2001 | Hodges et al. | |
| 6,299,757 B1 | 10/2001 | Feldman et al. | |
| 6,379,513 B1 | 4/2002 | Chambers et al. | |
| 6,413,410 B1 | 7/2002 | Hodges et al. | |
| 6,447,657 B1 | 9/2002 | Bhullar et al. | |
| 6,461,496 B1 * | 10/2002 | Feldman et al. | 205/777.5 |
| 6,475,372 B1 | 11/2002 | Ohara et al. | |
| 6,676,995 B2 | 1/2004 | Dick et al. | |
| 6,689,411 B2 | 2/2004 | Dick et al. | |
| 6,716,577 B1 | 4/2004 | Yu et al. | |
| 6,749,887 B1 | 6/2004 | Dick et al. | |
| 6,780,645 B2 | 8/2004 | Hayter et al. | |
| 6,830,934 B1 | 12/2004 | Harding et al. | |
| 2002/0053523 A1 | 5/2002 | Liamos et al. | |
| 2002/0084184 A1 | 7/2002 | Chambers et al. | |
| 2002/0150501 A1 | 10/2002 | Robertson et al. | |
| 2003/0150724 A1 * | 8/2003 | Kawanaka et al. | 204/403.02 |
| 2003/0180814 A1 | 9/2003 | Hodges | |
| 2004/0040866 A1 * | 3/2004 | Miyashita et al. | 205/777.5 |
| 2004/0050717 A1 | 3/2004 | Teodorczyk et al. | |
| 2004/0203137 A1 | 10/2004 | Hodges | |
| 2005/0013731 A1 | 1/2005 | Burke et al. | |
| 2006/0134713 A1 | 6/2006 | Hodges et al. | |
| 2010/0006452 A1 | 1/2010 | Rylatt et al. | |

FOREIGN PATENT DOCUMENTS

| | | |
|---|---|---|
| DE | 3103484 | 8/1982 |
| DE | 3708031 | 11/1987 |
| EP | 0290770 | 11/1988 |
| EP | 0400918 | 12/1990 |
| EP | 0-735363 | 10/1996 |
| EP | 0-609760 | 7/1998 |
| EP | 0-928967 | 3/2004 |
| EP | 1-081490 | 9/2004 |
| JP | 04343065 A | 11/1992 |
| JP | 05002007 | 1/1993 |
| JP | 6-222874 | 8/1994 |
| JP | 3167464 | 3/2001 |
| SU | 1351627 | 3/1986 |
| WO | WO-94/19684 | 9/1994 |
| WO | WO 94/29731 | 12/1994 |
| WO | WO 99/32881 | 7/1999 |
| WO | WO-99/60391 | 11/1999 |
| WO | WO-02/26129 | 4/2002 |

OTHER PUBLICATIONS

Niwa, et al. "Electrochemical Behavior of Reversible Redox Species at Interdigitated Array Electrodes with Different Geometries: Consideration of Redox Cycling and Collection Efficiency," Analytical Chemistry; Mar. 1990, vol. 62, No. 5, pp. 447-452.

USPTO, "Office Action," corresponding to related U.S. Appl. No. 11/138,080, mailed on Feb. 18, 2009, 19 pages.

USPTO, "Office Action," corresponding to related U.S. Appl. No. 11/138,080, mailed on Oct. 1, 2009, 21 pages.

USPTO, "Office Action," corresponding to related U.S. Appl. No. 11/138,080, mailed on Feb. 17, 2010, 22 pages.

USPTO, "Office Action," corresponding to related U.S. Appl. No. 11/138,080, mailed on Sep. 29, 2010, 23 pages.

USPTO, "Non-Final Office Action," corresponding to related U.S. Appl. No. 11/138,080, mailed on Jun. 10, 2011, 27 pages.

* cited by examiner

METHOD AND APPARATUS FOR ELECTROCHEMICAL ANALYSIS

RELATED APPLICATION

This application claims priority as a continuation-in-part to U.S. application Ser. No. 11/138,080, entitled "Method and Apparatus for Electrochemical Analysis," filed May 25, 2005, and which is hereby incorporated by reference in its entirety.

BACKGROUND OF THE INVENTION

Analyte detection in physiological fluids, e.g. blood or blood-derived products, is of ever increasing importance to today's society. Analyte detection assays find use in a variety of applications, including clinical laboratory testing, home testing, etc., where the results of such testing play a prominent role in diagnosis and management in a variety of disease conditions. In response to this growing importance of analyte detection, a variety of analyte detection protocols and devices for both clinical and home use have been developed.

One type of system allows people to conveniently monitor their blood glucose levels and includes a sensor (e.g., a disposable test strip), for receiving a blood sample from a user, and a meter that delivers an electrical impulse to the test strip and collects data during an electrochemical reaction to determine the glucose level in the blood sample. The test strip typically includes an electrical contact area at one end for electrically communicating with the meter and a sample chamber at the other end that contains reagents (e.g., glucose oxidase and a mediator) and electrodes. To begin the test, one end of the test strip is inserted into the meter and the user applies a blood sample to the sample chamber at the other end of the test strip. The meter then applies a voltage to the electrodes to cause a redox reaction and the meter measures the resulting current and calculates the glucose level based on the current. After the test, the test strip can be disposed.

Other biomedical devices include, for example, immunoassays that can detect the presence of an analyte of interest and/or measure analyte concentration. For example, when the analyte is a protein, the sensing element can be an antibody since the interaction of the antibody with the protein (antigen) is very specific. Such immunoassays usually fall into two categories: a "yes/no answer" obtained, e.g., by simple visual detection, or a concentration of the antigen determined by a quantitative method. Most of the quantitative methods involve expensive pieces of equipment such as scintillation counters (for monitoring radioactivity), spectrophotometers, spectrofluorimeters, and/or surface plasmon resonance instruments.

Accordingly, there is a need to provide analyte detection and measuring systems that are both inexpensive and simple enough to be suitable for home or field use.

SUMMARY OF THE INVENTION

Disclosed herein, are electrochemical systems and devices suited for use in the determination of a wide variety of analytes in a wide variety of samples, and are particularly suited for use in the determination of analytes in whole blood or derivatives thereof. As described, the system can comprise one or more sensors electrically connectable to a meter, the sensors having at least one reaction chamber for receiving a sample. The sensors can be adapted for mating with the meter during analysis such that the meter can send and receive electrical signals to/from the electrodes during analysis.

In one embodiment, the sensor can include multiple chambers adapted for a variety of reaction, including an electrochemical reaction cell and an immunological reaction cell. In one aspect, the sensor includes at least one electrochemical reaction cell, at least one immunological reaction cell, and laterally positioned electrical contact areas for mating with a meter. For example, in one embodiment, a sensor includes a first electrically conductive layer including a first electrode area, an opposing second electrically conductive layer including a second electrode area, and an insulating spacer layer positioned therebetween. The sensor can further include a sealing layer positioned adjacent to at least one of the first and second electrically conductive layers. The electrochemical reaction cell can also include spaced apart electrodes for performing an electrochemical analysis that are defined by an opening in the spacer layer and the first or second electrically conductive layers. The immunological cell can be defined by at least one of the first and second electrically conductive layers and the sealing layer.

Spaced laterally from the electrochemical reaction cell and the immunological cell are first and second electrical contact areas. In one aspect, at least a portion of one of the electrochemical reaction cell and the immunological cell is positioned between first and second electrical contact areas.

In one aspect, at least one of the electrochemical reaction cell and the immunological reaction cell extends from a proximal end of the spacer layer to a distal end of the spacer layer. For example, the immunological reaction cell can extend the full length of the sensor from a proximal sample ingress port in a proximal sidewall to a distal vent in a distal sidewall.

The electrical contact areas allow the sensor to electrically communicate with a meter. In one aspect, the first electrical contact area is positioned on a first surface of the sensor and the second electrical contact area is positioned on a second surface of the sensor. The electrical contact areas can also be positioned on the distal portion of the sensor such that they are spaced from the proximal end of the sensor.

The electrochemical reaction cell can include at least first and second electrodes for electrochemically detecting the presence or absence of an electrochemical species. In one aspect, the sensor can include electrochemical reagents. For example, the electrochemical cell can include electrochemical reagents. The immunological cell can include immunological species. In one exemplary embodiment, the immunological cell includes an antigen and/or an antibody that can react with an analyte of interest.

In another aspect, the sensor includes at least one connective flap for mating with an adjacent sensor in an array of sensors. In one exemplary embodiment, the connective flap is a portion of a connective link that mates adjacent sensors and is formed by a portion of the spacer layer that extends beyond the first and second electrically conductive layers. The sensor can include connective flaps positioned at the proximal end for mating with a proximally positioned sensor and at the distal end for mating with a distally positioned sensor.

Further described herein is an array of sensors held together by connective flaps. In one aspect, the flaps are flexible such that individual sensors can pivot with respect to one another. In another aspect, connective flaps allows for storage of the array in a folded configuration. In use, the subject sensors can be positioned within a sensor dispenser in a folded configuration and individually dispensed for use in determining an analyte concentration value in a physiological sample.

In another embodiment of the sensor described herein, more than two cells are provided. The sensor can include a pre-chamber for holding a portion of a sample, an immunological cell, and an electrochemical reaction cell. For example, in one embodiment, a sensor includes a first electrically conductive layer including a first electrode area, an opposing second electrically conductive layer including a second electrode area, and an insulating spacer layer positioned therebetween. The sensor can further include a sealing layer positioned adjacent to at least one of the first and second electrically conductive layers. The electrochemical reaction cell can be defined by an opening in the spacer layer and the first and second electrically conductive layers, while the immunological cell can be defined by a second opening in the spacer layer and the first and second electrically conductive layers. The pre-chamber can be defined by one of the first and second electrically conductive layers and the sealing layer.

In yet another embodiment of the multi-chambered sensor disclosed herein, a third electrical contact area is provided for sensing if/when the pre-chamber and or the immunological cell is filled with a sample. In one aspect, an electrical circuit between the third electrical contact area and one of the first and second electrical contact areas is closed when a sample fills the immunological cell.

DETAILED DESCRIPTION OF ILLUSTRATIVE EMBODIMENTS OF THE INVENTION

Figure 1A:
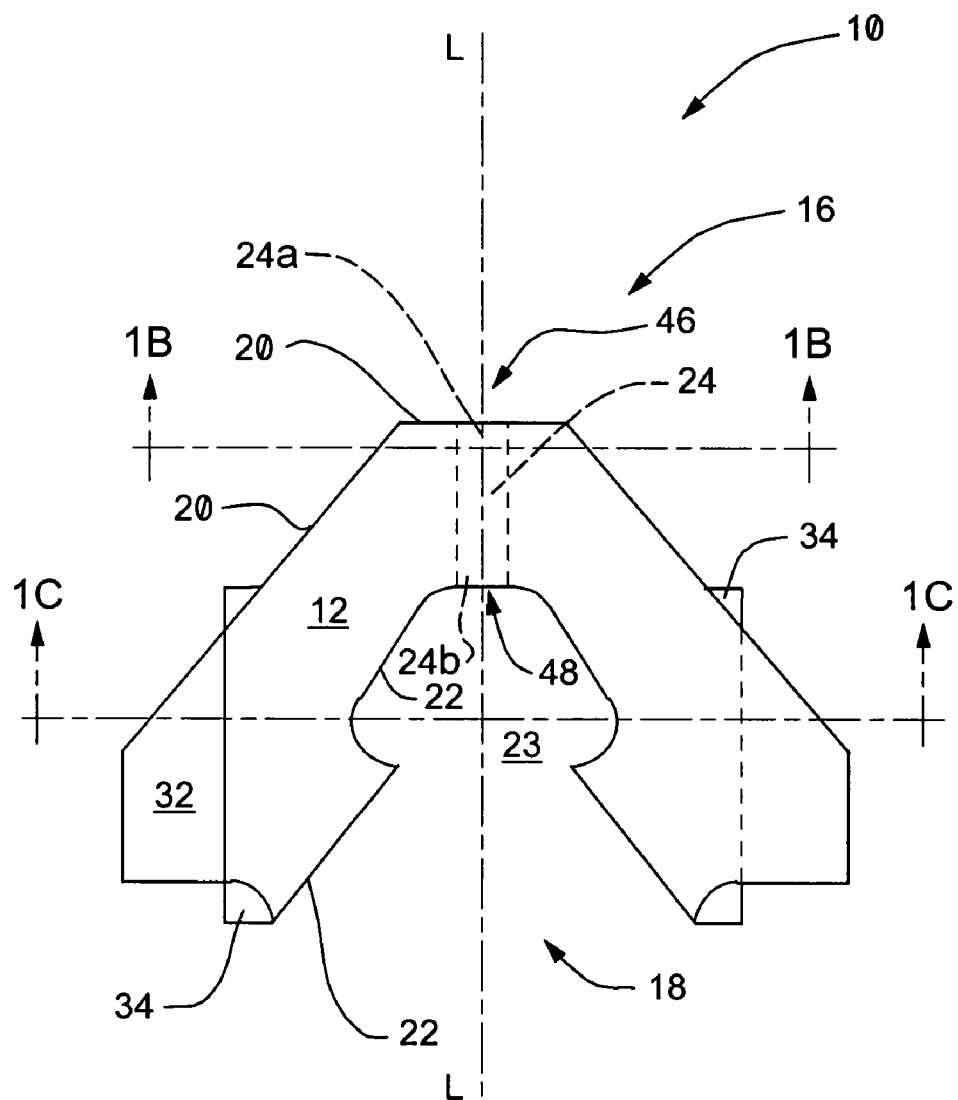
FIG. 1A shows a top view of one embodiment of the sensor described herein.
Figure 1B:
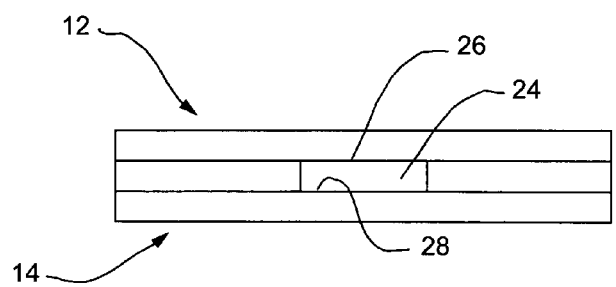
FIG. 1B is a cross sectional view of the sensor of FIG. 1A along the line B-B.

Described herein are sensors that can include a reaction chamber for receiving a sample and laterally positioned electrical contact areas for mating with a meter. Further described herein is a multi-chambered sensor having laterally positioned electrical contact areas, the sensor including a first chamber adapted for an immunological reaction and a second chamber adapted to detect an electrochemical reaction. In use, the multi-chambered device allows for a simple and inexpensive immunoassay.

In a first embodiment illustrated by FIGS. 1A through 1D, a sensor 10 has a generally planar configuration comprising a top surface 12, a bottom surface 14, and a longitudinal axis L extending between a proximal end 16 and a distal end 18. The sensor further includes a proximal sidewall 20 and a distal sidewall 22. The thickness of sensor 10 can vary across its length and/or width, and as shown in the sectional side views of FIGS. 1B and 1C, sensor 10 can comprise multiple layers laminated together.

Positioned between top and bottom surfaces 12, 14, sensor 10 includes an electrochemical reaction cell 24, having electrodes 26, 28 (FIG. 1B) positioned therein, for electrochemically analyzing a sample. In one aspect, reaction cell 24 extends in the longitudinal direction to define an elongate reaction cell. For example, in FIG. 1A reaction cell 24 is positioned along longitudinal axis L and extends between proximal end 24a and distal end 24b. In one embodiment, the reaction cell runs the length of sensor 10 from proximal sidewall 20 to distal sidewall 22. Alternatively, reaction cell 24 can extend longitudinally along a portion of the sensor such that the reaction cell is shorter than the full length of the sensor.

Physiological fluid can be delivered to reaction cell 24 through a sample ingress port 46. In one aspect, the proximal sidewall 20 of sensor 10 includes sample ingress port 46 for delivery of a sample into reaction cell 24. For example, the proximal end 24a of reaction cell 24 can be open to the atmosphere. In another aspect, the reaction cell can include a second opening 48 that allows for the entrance of a sample and/or the egress of gas. For example, second opening 48 can act as a vent that allows air within the reaction cell to escape as a sample is delivered through sample ingress port 46. Second opening 48 can be positioned at the distal end 24b of reaction cell 24. In one aspect, second opening 48 is at the distal sidewall 22 of sensor 10 and reaction cell 24 extends the full length of sensor 10 from proximal sidewall 20 to distal sidewall 22.

Figure 2A:
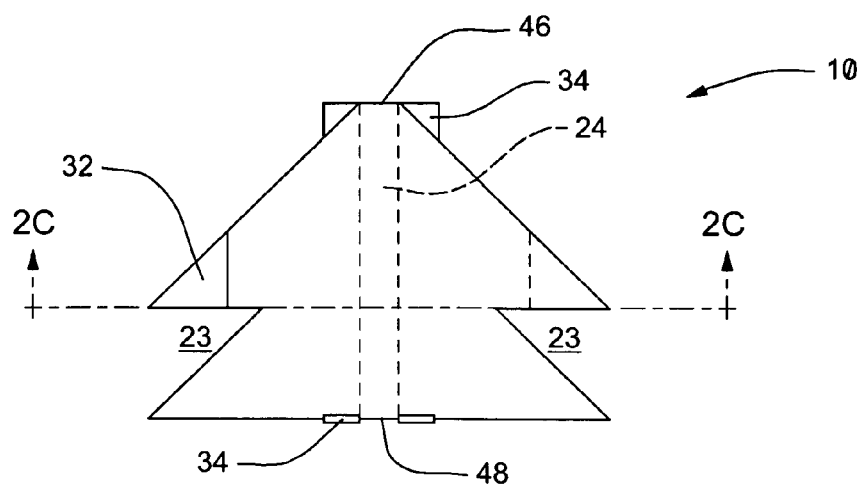
FIG. 2A is a top view of another embodiment of the sensor described herein.
Figure 2B:
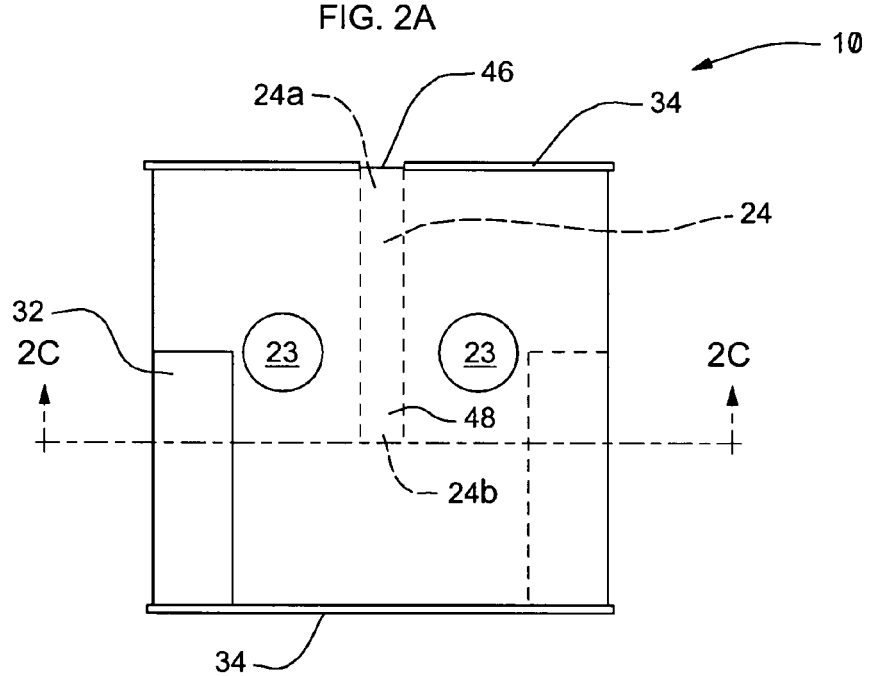
FIG. 2B is a top view of yet another embodiment of the sensor described herein.

In an alternative embodiment, reaction cell 24 extends less than the full length of the sensor and second reaction cell opening 48 is positioned proximally to the distal end 18 of the sensor (FIG. 2B). For example, an opening 48 could be formed through the top or bottom surface of sensor 10.

Spaced laterally from the central longitudinal axis L are a first electrical contact area 30 and a second electrical contact area 32 that allow for electrical communication between a meter (e.g., blood glucose meter) and the reaction cell 24. In use, a meter can mate with sensor 10 such that the contact areas 30, 32 are electrically connected to a circuit within the meter. The first and second electrical contact areas, which are electrically connected to the electrodes 26, 28 within reaction cell 24, allow the circuit to deliver an electric potential to the electrodes.

Figure 1C:
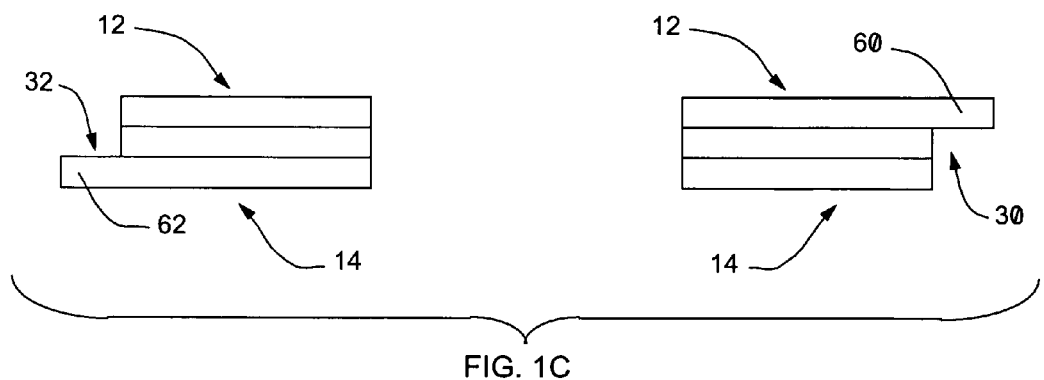
FIG. 1C is a cross sectional view of the sensor of FIG. 1A along the line C-C.

The first and second electrical contact areas 30, 32, in one aspect, define a portion of the sensor surface that is spaced laterally with respect to the longitudinal axis L of sensor 10. FIG. 1C illustrates a sectional side view of sensor 10 of FIG. 1A along line C-C that shows first and second electrical contact areas 30, 32. The contact areas are positioned adjacent to the outer lateral edges of sensor 10, while the longitudinally reaction cell 24 (FIG. 1B) is positioned along the longitudinal axis. In use, the contact areas can mate with laterally spaced contactors on a meter while the longitudinal reaction cell is available for receiving a sample.

The first and second electrical contact areas are, in one embodiment, positioned on opposite surfaces of sensor 10. For example, the first electrical contact area 30 can be positioned on bottom surface 14 and the second electrical contact area 32 can be positioned on the top surface 12 (FIG. 1C).

To facilitate mating with a meter, the first and second electrical contact area can be positioned in a variety of locations. For example, contact areas 30, 32 in FIG. 1A are positioned at the distal end of sensor 10. In one embodiment, contact areas 30, 32 are positioned distally with respect to the proximal end 16 of sensor 10, and in another embodiment, the contact areas 30, 32 are positioned distally with respect to reaction cell 24 of sensor 10. Alternatively, contact areas 30, 32 could extend the full longitudinal length of the sensor 10 or extend only over a proximal portion of the sensor.

Figure 1D:
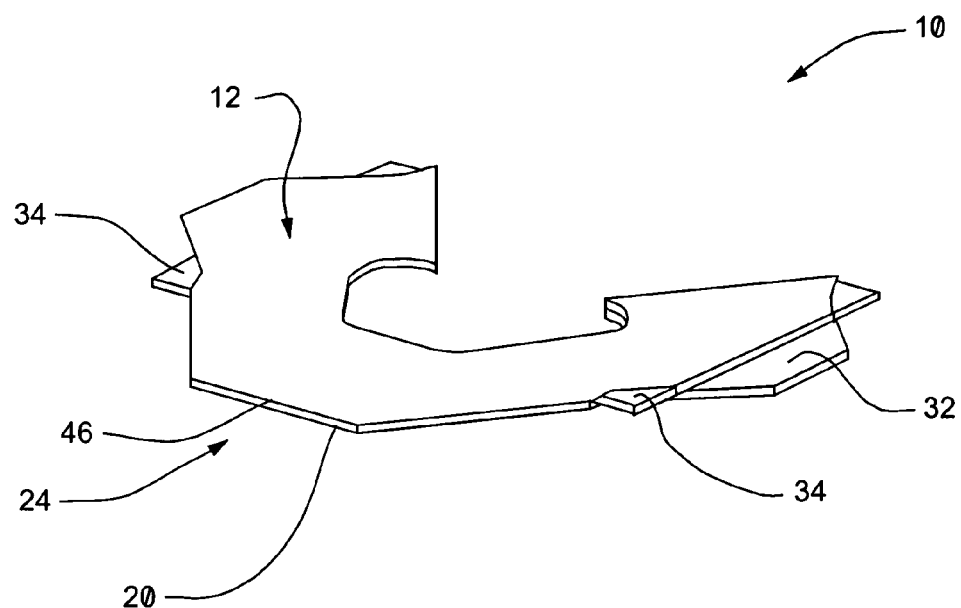
FIG. 1D is a perspective view of the sensor of FIG. 1A.
Figure 1E:
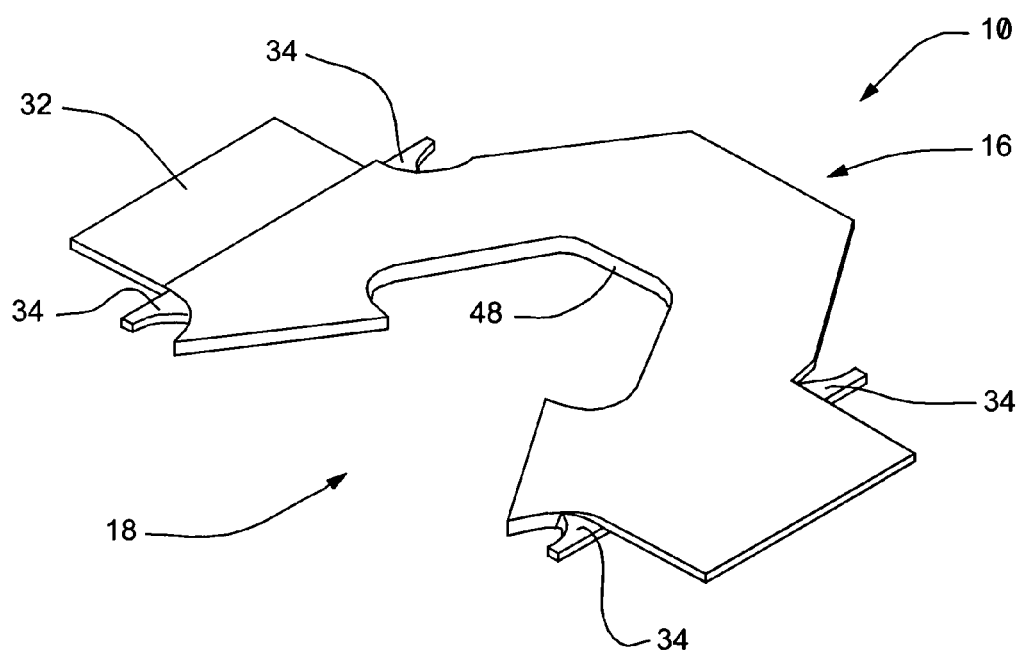
FIG. 1E is a perspective view of another embodiment of the sensor of FIG. 1A.

In one embodiment, electrical contact areas 30, 32 have a tapered proximal end as shown in FIG. 1D. Alternatively, electrical contact areas 30, 32 could have a rectangular configuration as shown in FIG. 1E. One skilled in the art will appreciate that electrical contact areas 30, 32 can have a variety of shapes and sizes that will allow the sensor 10 to electrically communicate with a meter.

Sensor 10 can further include linking features that allow sensor 10 to mate with an adjacent sensor to create an array of sensors. In one embodiment, the linking features include connective flaps 34 that extend from the edge of the sensor. Each connective flap represents one half of a link that can mate two adjacent sensors. Sensor 10 can include multiple flaps 34 to provide multiple links to an adjacent sensor, and in one embodiment sensor 10 includes two pairs of spaced apart flaps. As shown in FIG. 1A, a first pair of flaps extends from the proximal sidewall 20 and a second pair of flaps extends from the distal sidewall 22.

Figure 2C:
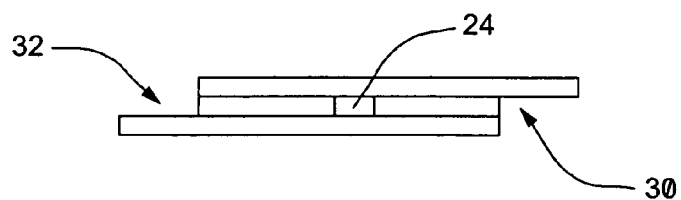
FIG. 2C is a cross sectional view of the sensors illustrated in FIGS. 2A and 2B along the line C-C.

Sensor 10, in one embodiment, has a generally "V" shape as illustrated in FIG. 1A through 1D. Sensor 10 can alternatively have another shape as illustrated in FIGS. 2A through 2C. For example, FIG. 2A illustrates a "tree" configuration including longitudinally extending reaction cell 24, lateral spaced connection areas 30, 32, and connective flaps 34. FIG. 2B illustrates a rectangular configuration including longitudinally extending reaction cell 24, lateral spaced connection areas 30, 32, and a connective flaps 34.

Regardless of the sensor's geometric configuration, sensor 10 can include mating features that facilitate mating sensor 10 with a meter and/or a sensor dispenser. For example, the sensor disclosed in FIG. 1A includes a central opening 23 between the legs of the "V" that can receiving an actuating portion of a sensor dispenser and/or a meter. In one embodiment, opening 23 is positioned between the contact areas 30, 32 as shown in FIG. 1C. The meter and/or sensor dispenser can use opening 23 to hold and/or advance the sensor. Other mating features, such a lateral openings 23 in the sides of the sensor illustrated in FIG. 2A, or apertures 23 extending through the sensor illustrated in FIG. 2B can alternatively be used to mate with a sensor dispenser and/or a meter.

Figure 3:
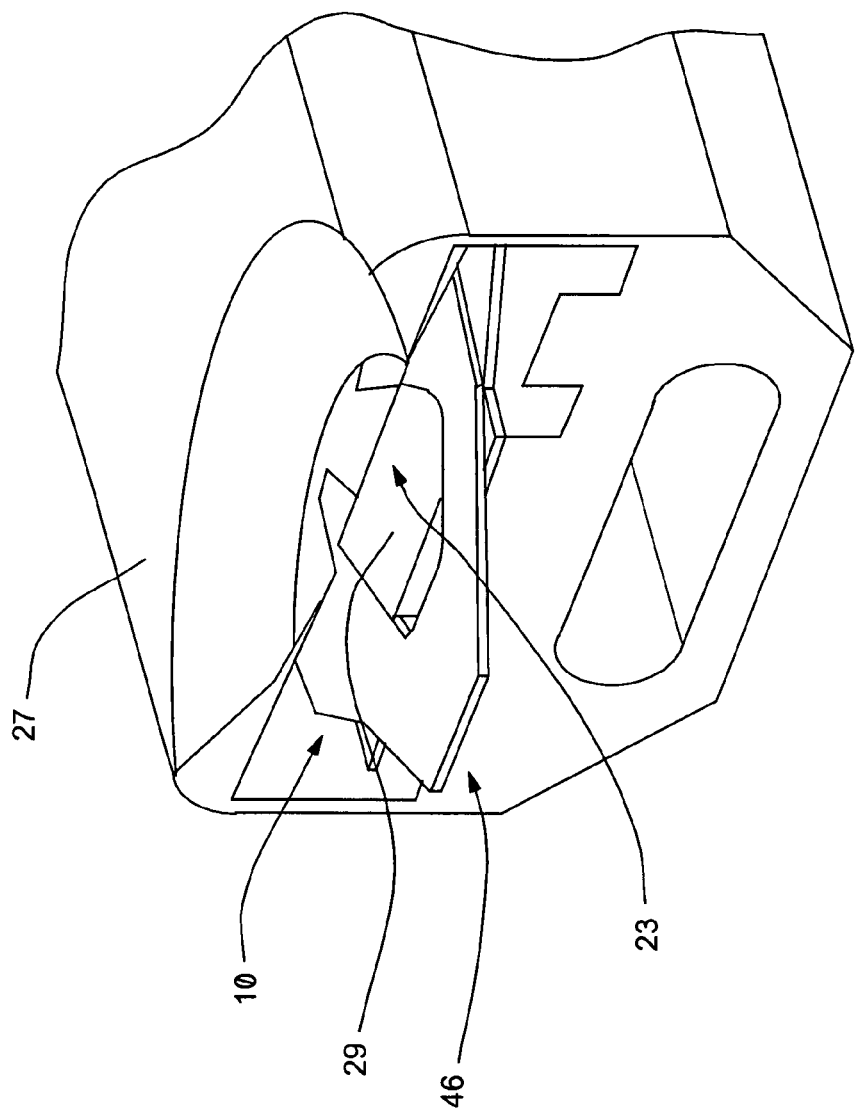
FIG. 3 is a perspective view of one embodiment of the sensor described herein positioned within a meter.

FIG. 3 illustrates the sensor of FIG. 1A positioned within a meter 27. As shown, a retention post 29 can mate with central opening 23 to hold sensor 10 within meter 27. One skilled in the art will appreciate that sensor 10 can mate with a meter and/or sensor dispenser via a variety of opening and/or surface features. While the sensor mating feature(s) have been described with respect to sensor 10 illustrated in FIGS. 1A through 3, any of the sensors described herein (e.g., sensors 10, 110, 210) can include mating features for mating with a meter.

Figure 4A:
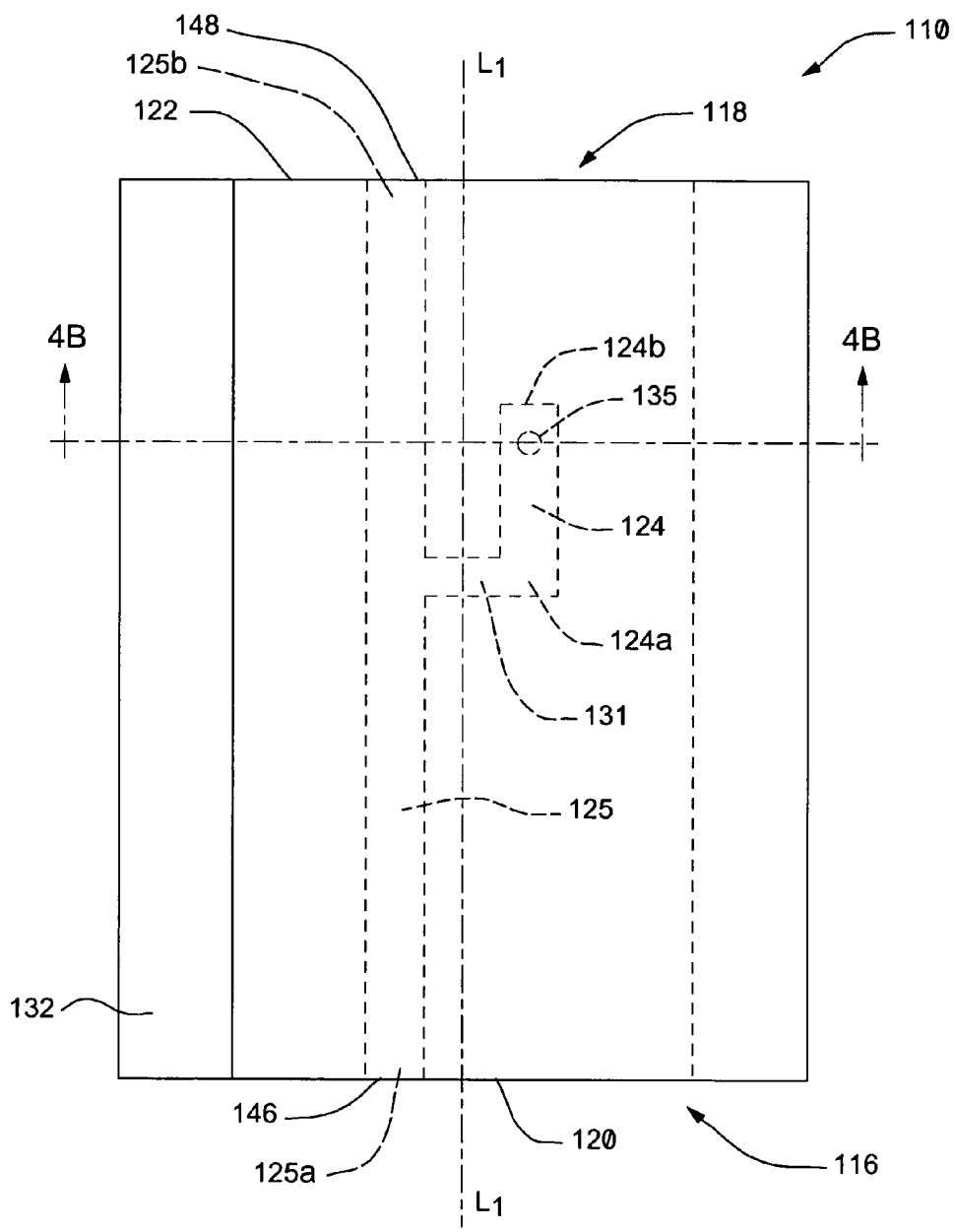
FIG. 4A is a top view of one embodiment of a two-chambered sensor described herein.
Figure 4B:
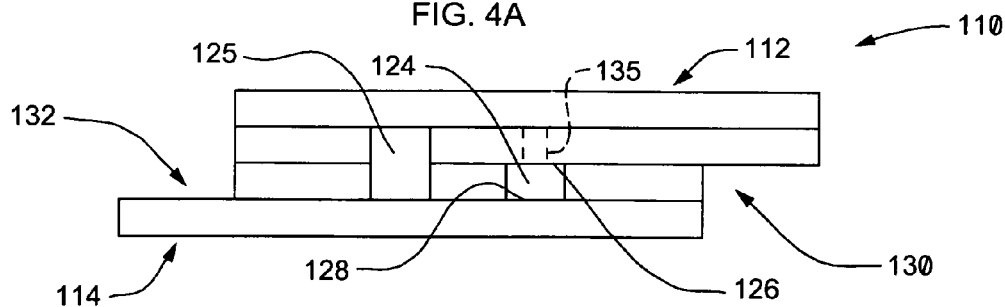
FIG. 4B is a cross sectional view of the sensor of FIG. 4A along the line B-B.

In another embodiment, a multi-chambered sensor is disclosed herein. FIGS. 4A and 4B illustrate sensor 110 having a first and a second cells 125, 124 and laterally spaced electrical contact areas 130, 132. A multi-chambered sensor can be utilized to analyze a variety of samples, and in particular, allows the electrochemical capabilities of the sensor to be combined with an additional reaction step. In one aspect, an electrochemical reaction and an immunological reaction can both be performed with sensor 110. For example, at least one of first and second cells 125, 124 can include electrodes and act as an electrochemical reaction and/or detection chamber like electrochemical reaction chamber 24 described above. The other chamber can be used, in one embodiment, as an immunological reaction chamber. For example, first cell 125 can be an immunological chamber. The immunological chamber can include a variety of immunological reagents and be adapted to react with or react as a result of the presence of, a variety of analytes. Exemplary immunological chambers are disclosed, for example, in U.S. patent application Ser. No. 10/830,841, entitled "Immunosensor" and Ser. No. 10/105,050 entitled "Direct Immunosensor Assay" both of which are hereby incorporated by reference in their entirety.

In one aspect, sensor 110 has a generally planar configuration (similar to sensor 10) including a top surface 112, a bottom surface 114, and a longitudinally extending axis $L_1$ extending between a proximal end 116 and a distal end 118. Sensor 110 can further include a proximal sidewall 120 and a distal sidewall 122. The thickness of sensor 110 can vary across its length and/or width, and as shown in FIG. 4B, sensor 110 can comprise three or more layers laminated together. In one aspect, sensor 110 includes four or more layers.

Positioned between top and bottom surfaces 112, 114, sensor 110 can include an electrochemical reaction cell 124, having electrodes 126, 128 (FIG. 4B) positioned therein, for electrochemically analyzing a sample. One skilled in the art will appreciate that while cell 124 is referred to as an electrochemical "reaction" cell, a portion of the electrochemical reaction can occur in a different cell, such as for example, in cell 125. In one aspect, reaction cell 124 extends in the longitudinal direction to define an elongate reaction cell. Alternatively, reaction cell 124 can have a different orientation, such as for example, reaction cell 124 can be positioned at an angle with respect to cell 125 or with respect to longitudinal axis $L_1$. In addition, one of ordinary skill in the art will appreciate the cell 124 can have a variety of shapes, such as, for example rectangular, circular, or irregular. In one embodiment, as shown in FIG. 4A, reaction cell 124 can run less than the full length of sensor 110. For example, in FIG. 4A reaction cell 124 run parallel to longitudinal axis $L_1$ and extends between a proximal end 124a and a distal end 124b.

As shown in FIG. 4A, immunological cell 125, in one aspect, runs parallel to longitudinal axis $L_1$ and can extend the full length of the sensor from proximal sidewall 120 to distal sidewall 122. In another aspect, cell 125 can be positioned at an angle with respect to longitudinal axis $L_1$. One skilled in the art will appreciate that cells 124, 125 can have a variety of configurations and orientations that allow lateral positioning of electrical contacts areas 130, 132.

In use, physiological fluid can first be delivered to cell 125 through a sample ingress port 146. In one aspect, the proximal sidewall 120 of sensor 110 includes sample ingress port 146 for delivery of a sample into first cell 125. For example, a proximal end 125a of cell 125 can be open to the atmosphere. In another aspect, the first cell can include a second opening 148 that allows for the entrance of a sample and/or the egress of gas. For example, second opening 148 can act as a vent that allows air within the first cell to escape as a sample is delivered through sample ingress port 146. Second opening 148 can be positioned at the distal end 125b of first cell 125. In one aspect, second opening 148 is in the distal sidewall 122 of sensor 110 and first cell 125 extends the full length of sensor 110 from proximal sidewall 120 to distal sidewall 122.

In an alternative embodiment, first cell 125 can extend less than the full length of the sensor and second cell opening 148 can be positioned proximally to the distal end 118 of the sensor (not illustrated). For example, an opening 148 could be formed through the top or bottom surface of sensor 110.

Figure 5A:
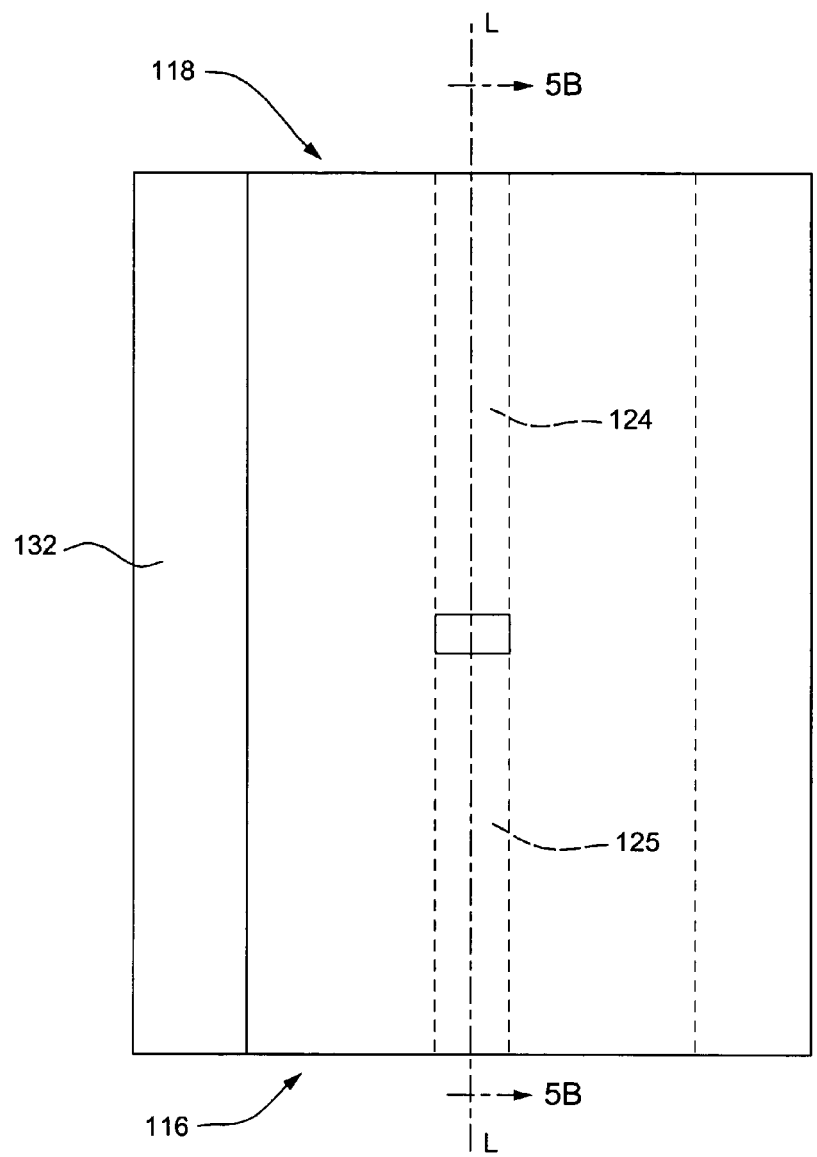
FIG. 5A is a top view of another embodiment of the two-chambered sensor described herein.
Figure 5B:
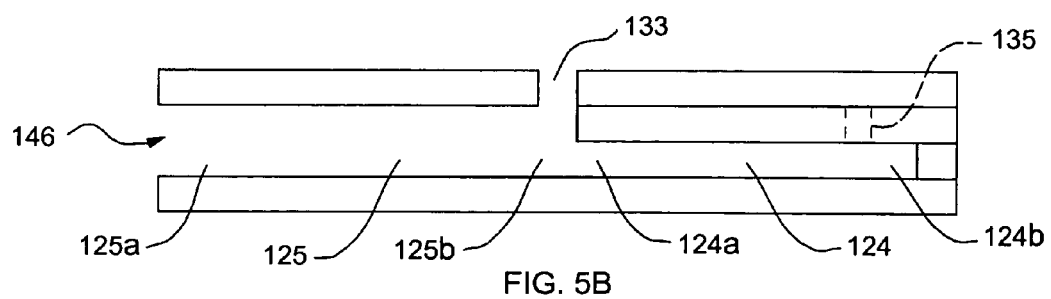
FIG. 5B is a cross sectional view of the sensor of FIG. 5A along the line B-B.

In another embodiment of sensor 110, cells 125, 124 are positioned in an end-to-end configuration. As shown in FIGS. 5A and 5B, cells 125, 124 can be positioned along the central longitudinal axis $L_1$ of sensor 110 and extend from proximal end 116 of sensor 110 toward distal end 118. In one embodiment, cells 125, 124 run the full length of sensor 110. Alternatively, end 124b of cell 124 can end proximal to the distal end of sensor 110.

As shown in FIG. 5B, cell 125 includes sample ingress 146 at end 125a and a vent 133 at end 125b. As sample is delivered to cell 125, vent 133 allow displaced air to escape. A passageway 131 (i.e., an opening) between cells 124, 125 can allow a fluid sample to pass from cell 125 to cell 124.

In one embodiment of sensor 110 (as illustrated in FIGS. 4A though 5B), a sample is first delivered to immunological reaction cell 125 and then moved to electrochemical reaction cell 124 via capillary action. Capillary action can be used to first draw sample into cell 125 and then a second, stronger capillary force can move sample into cell 124. For example, cell 125 can be configured such that when a sample is brought into contact with sample ingress opening 146, the sample is wicked or drawn into cell 125. Once sample is positioned within cell 125, a vent in cell 124 can be opened to draw sample into cell 124 with capillary action.

As shown in FIGS. 4A through 5B, cell 125 is open at ends 125a, 125b so that when a sample is delivered to opening 146, air within the cell can be displaced. However, cell 124 is closed at end 124b, such that when cell 125 fills with sample, the sample does not fill cell 124. The closed end of cell 124 can trap air in the cell and substantially prevent it from filling with sample. To fill cell 124, a vent 135 is opened to the atmosphere to allow the trapped air to escape.

One skilled in the art will appreciate that the capillary force required to fill cells 124, 125 with sample can be created by adjusting a variety of characteristics. For example, the dimensions of cells 124, 125 can be such that cell 124 has a greater capillary force than cell 125. In one aspect, cell 125 has a greater cell height than cell 124. In addition, or alternatively, the surface features of cells 124, 125 can be adjusted to create a differential in capillary force between the cells. For example, cells 124, 125 could have equal cell height, but cell 124 could be filled with a substance, such as a mesh, to create a greater capillary force in cell 124. In addition, the volume of cell 125 is typically chosen so as to be at least equal to and preferably larger than the volume of cell 124, so that cell 124 can be substantially filled with sample.

The process of moving sample from cell 125 to cell 124 can include opening vent 135 as mentioned above. In one aspect, a user can create vent 135 by puncturing a hole through top surface 112 or bottom surface 114. Vent 135 can alternatively be opened by means of a solenoid in the sensor. In another embodiment, vent 135 can include a pre-formed vent hole though at least one of top surface 112 and bottom surface 114. A cover can seal the vent hole until it is punctured to open vent 135. In still another embodiment, vent 135 can be created by breaking away a portion of sensor 110. For example, distal end 118 of sensor 110 in FIG. 5A could be broken away to expose end 124b of cell 124. To facilitate breaking away a portion of sensor 110, the sensor can include a weakened area such as a perforation (not illustrated).

In another embodiment of the sensor disclosed herein, a three-chambered sensor provided. FIGS. 6A through 6D illustrate sensor 210 having first, second, and third cells 221, 224, 225 and laterally spaced electrical contact areas 230, 232. Sensor 210 can include an electrochemical reaction chamber, an immunological reaction chamber, and a pre-chamber for filling with a sample. The pre-chamber allows for storage of sample prior to filling the electrochemical chamber. In one aspect, at least one of first, second, and third cells 225, 224, 221 can include electrodes and act as an electrochemical reaction and/or detection chamber like electrochemical reaction chambers 24, 124 described above. One of the other chambers can be used, in one embodiment, as an immunological reaction chamber similar to cell 125 described above. The third cell can be a pre-chamber. For example, cell 221 can be a pre-chamber, cell 225 can be an immunological chamber, and cell 224 can be an electrochemical reaction chamber.

Figure 6A:
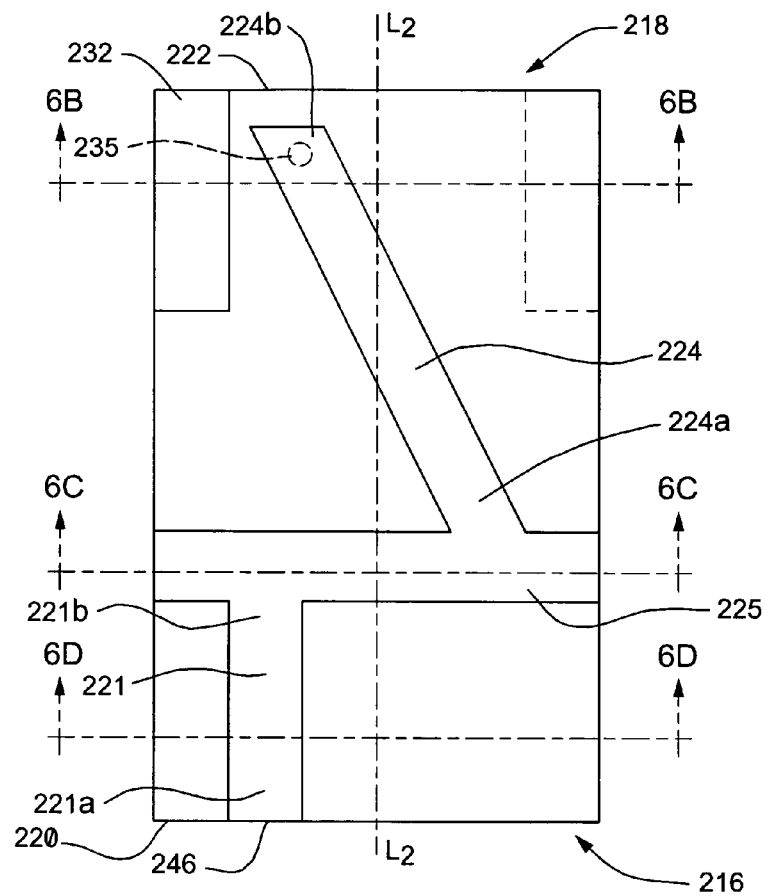
FIG. 6A is a top view of a three-chambered sensor described herein.
Figure 6B:
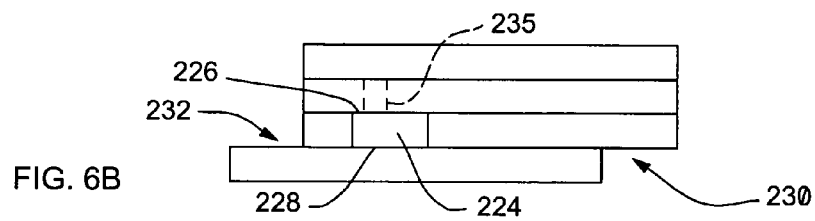
FIG. 6B is a cross sectional view of the sensor of FIG. 6A along the line B-B.
Figure 6C:
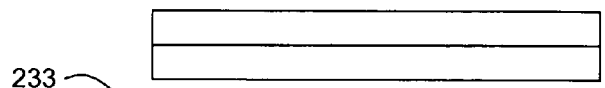
FIG. 6C is a cross sectional view of the sensor of FIG. 6A along the line C-C.
Figure 6D:
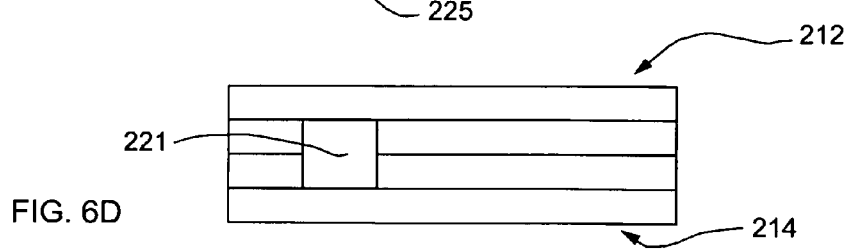
FIG. 6D is a cross sectional view of the sensor of FIG. 6A along the line D-D.

In one aspect, sensor 210 has a generally planar configuration (similar to sensors 10, 110) including a top surface 212, a bottom surface 214, and a longitudinally extending axis $L_2$ extending between a proximal end 216 and a distal end 218. Sensor 210 can further include a proximal sidewall 220 and a distal sidewall 222. The thickness of sensor 210 can vary across its length and/or width, and as shown in FIGS. 6B through 6D, and sensor 210 can comprise three or more layers laminated together.

Positioned between top and bottom surfaces 212, 214, sensor 210 can include an electrochemical reaction cell 224, having electrodes 226, 228 (FIG. 6B) positioned therein, for electrochemically analyzing a sample. In one aspect, reaction cell 224 is an elongate reaction cell that is located toward the center of sensor 210 with respect to electrical contact areas 230, 232. As shown in FIG. 6A, cell 224 can be positioned at an angle with respect to cell 225 and/or with respect to longitudinal axis $L_2$. In one embodiment, as shown in FIG. 6A, reaction cell 224 can run between immunological reaction cell 225 and a point proximal to distal end 218 of sensor 210, and extend between a proximal end 224a and a distal end 224b.

In use, physiological fluid can be delivered to cell 221, defining a pre-chamber, through a sample ingress port 246. Sample ingress port 246 can be positioned in proximal sidewall 220 of sensor 210. For example, a proximal end 221a of cell 221 can be open to the atmosphere. Cell 221 can include a second opening at distal end 221b defining a passage way between cell 221 and cell 225.

In one aspect, the cell 225 can include at least one vent 233 such that as sample is delivered to cell 221 (and cell 225) air displaced by the sample can escape from the chambers. For example, as shown in FIG. 6C, immunological reaction cell 225 can extend across sensor 210 and include vent 233 in at least one lateral edge of sensor 221. In an alternative embodiment, cell 225 can include vent 233 through at least one of top and bottom surfaces 112, 114.

When a sample is delivered to cell 221, capillary action can draw the sample into cell 221 and cell 225. For example, as shown in FIGS. 6B and 6C, cell 221 can have a height that is greater than cell 225, and the capillary force created by cell 225 can be greater than cell 221. In use, a sample delivered to sample ingress opening 246 can fill cells 221, 225.

One skilled in the art will appreciate that cells 221, 225 can have a variety of configurations and orientations. For example, cells 221, 225 can be positioned at angle with respect to one another or alternatively could extend along the longitudinal axis $L_2$ of sensor 210 in an end-to-end configuration (not illustrated).

In one embodiment, electrochemical reaction 224 can be open to cell 225 at proximal end 224a and closed at distal end 224b. As sample is delivered to pre-chamber cell 221 and immunological reaction cell 225, sample is not drawn into cell 224. The closed end of cell 224 can trap air in the cell and substantially prevent it from filling with sample. To fill cell 224, a vent 235 is opened to the atmosphere to allow the trapped air to escape.

One skilled in the art will appreciate that the capillary force required to fill cells 221, 225, 224 with sample can be created by adjusting a variety of characteristics. For example, the dimensions of cells 221, 225, 224 can be such that cells 224, 225 have a greater capillary force than cell 221. In one aspect, cell 221 has a greater cell height than cells 225, 224. In addition, or alternatively, the surface features and characteristics of cells 225 and/or 224 can be adjusted to create a differential in capillary force between the cells.

The process of moving sample from cell 225 to cell 224 can include opening vent 235. For example, a user can create vent 235 by puncturing a hole through at least one of top surface 112 and bottom surface 114. Vent 235 can alternatively be opened by means of a solenoid in the sensor. In another embodiment, vent 235 can include a pre-formed vent hole though at least one of top surface 212 and bottom surface 214. A cover can seal the vent hole until it is punctured to open vent 235. In still another embodiment, vent 235 can be created by breaking away a portion of sensor 210. For example, distal end 218 of sensor 210 in FIG. 6A could be broken away to expose end 224b of cell 224.

Sensors 110, 210, as illustrated in FIG. 4A through 6D, can include electrical contact areas as discussed with respect to sensor 10 above. In use, a meter can mate with sensors 110, 210 such that the contact areas 130, 132, 230, 232 are electrically connected to a circuit within the meter. The first and second electrical contact areas 130, 132, 230, 232, which are electrically connected to the electrodes 126, 128, 226, 228 within reaction cell 124, 224, allow the circuit to deliver an electric potential to the electrodes.

The first and second electrical contact areas 130, 132, 230, 232, in one aspect, define a portion of the sensor surface that is spaced laterally with respect to the longitudinal axis $L_1$ of sensors 110, 210. For example, contact areas can be positioned adjacent to the outer lateral edges of sensor 110, 210, while cells 124, 224 are positioned toward the center of sensors 110, 210. In use, the contact areas can mate with laterally spaced contactors on a meter while the longitudinal reaction cell is available for receiving a sample.

The first and second electrical contact areas are, in one embodiment, positioned on opposite surfaces of sensor 110, 220. For example, the first electrical contact area 130, 230 can be positioned on bottom surface 114, 214 and the second electrical contact area 132, 232 can be positioned on the top surface 112, 212.

Sensors 10, 110, 210 in one embodiment, can be formed from a multi-layer laminate including a first electrically conductive layer, a second electrically conductive layer, and an insulating spacer layer. The electrically conductive layers can comprise an electrically conductive material and optionally an insulating substrate. A spacer layer positioned between the electrically conductive layers, can comprise an insulating material, and in one aspect, binds the layers of the laminate together. In addition, the sensor can include additional layers, such as a sealing layer, to provide cells of different heights. One skilled in the art will appreciate that the spacer layer, the first electrically conductive layer, the second electrically conductive layer, and/or the sealing layer can comprise more than a single layer (e.g., the layers could comprise multiple layers of insulation, adhesives, etc.).

Figure 7A:
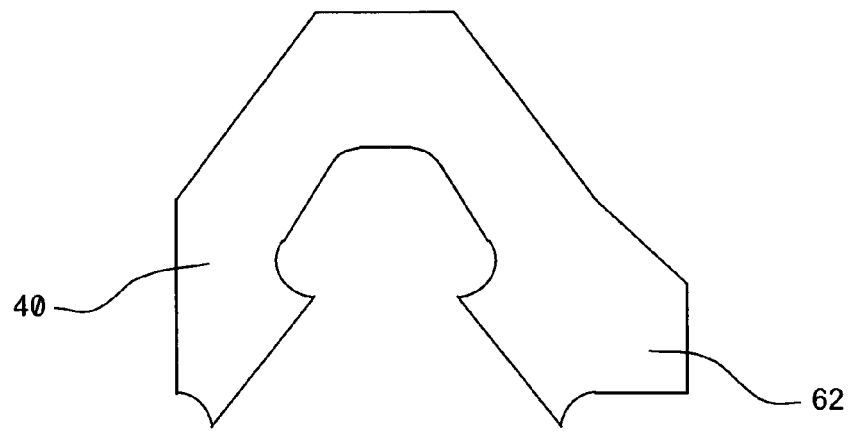
FIG. 7A is a top view of the first electrically conductive layer of the sensor of FIG. 1A.
Figure 7B:
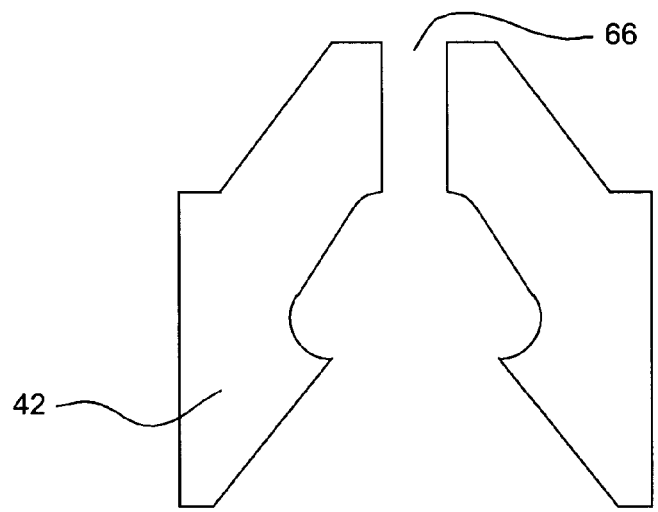
FIG. 7B is a top view of a spacer layer of the sensor of FIG. 1A.
Figure 7C:
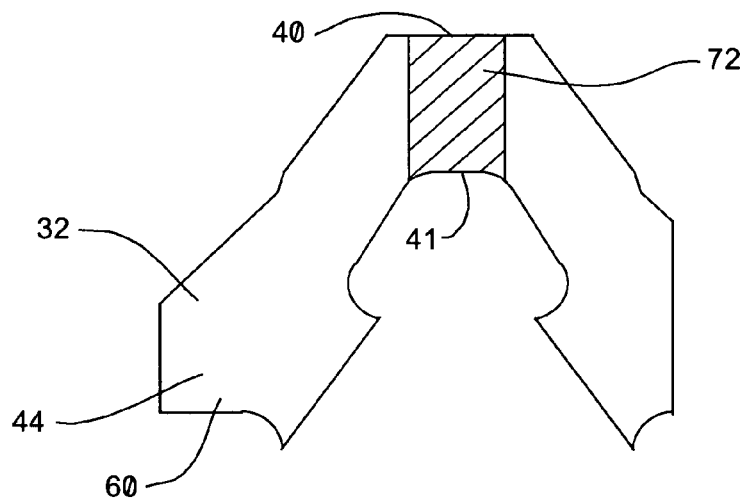
FIG. 7C is a top view of a second electrically conductive layer of the sensor of FIG. 1A.

FIGS. 7A through 7C illustrate exemplary layers that can be combined to form sensor 10. For example, FIGS. 7A and 7C illustrate the first and second electrically conductive layers 40, 44, and FIG. 7B illustrates spacer layer 42. FIGS. 8A through 9D illustrate four exemplary layers used to form multi-chambered sensor 110 (of FIGS. 4A and 4B) and multi-chambered sensor 210 (of FIGS. 6A through 6D). First electrically conductive layers 140, 240 of sensors 110, 210 are illustrated in FIGS. 8B, 9B respectively, and the second electrically conductive layers 144, 244 are illustrated in FIGS. 8D, 9D respectively. Spacer layers 142, 242, configured for use in sensors 110, 210, are illustrated in FIGS. 8C, 9C respectively. The multi-chambered sensor 110, 210 can include an additional sealing layer 145, 245 illustrated in FIGS. 8A, 9A respectively.

The first and second electrically conductive layers can provide the conductive surface required for the first and second electrodes and the contact areas. In one aspect, first electrode 26, 126, 226 and first contact 30, 130, 230 are positioned on the first electrically conductive layer 40, 140, 240 and the second electrode 28, 128, 228 and second contact area 32, 132, 232 are positioned on the second electrically conductive layer 44, 144, 244. The first and second electrically conductive layers can further provide an electrically conductive track between the first and second electrodes and the first and second contact areas, respectively, to electrically connect the electrodes to the electrical contact areas.

In one embodiment, first and/or second electrically conductive layers may be a conductive material such as gold, palladium, carbon, silver, platinum, iridium, doped tin oxide, and stainless steel. In addition, the electrically conductive layers can be formed by disposing a conductive material onto an insulating sheet (not shown) by a sputtering or a screen-printing process. In one exemplary embodiment, one electrically conductive material may be sputtered gold and the other conductive material can be sputtered palladium. Suitable materials that may be employed as the insulating sheet on which the electrically conductive material is deposited include plastic (e.g. PET, PETG, polyimide, polycarbonate, and/or polystyrene), silicon, ceramic, glass, and combinations thereof.

Spacer layer 42, 142, 242 can comprise a variety of insulting (non-electrically conductive or minimally electrically conductive) materials. Exemplary spacer materials can include, for example, plastics (e.g. PET, PETG, polyimide, polycarbonate, and/or polystyrene), silicon, ceramic, glass, and combinations thereof. Spacer layer 42, 142, 242 can also include, or be formed substantially of, an adhesive.

An opening in the spacer layer provides an area for reaction cell 24, 124, 224. In one aspect, an aperture in spacer layer 42, 142, 242 defines the sidewalls of the reaction cell. The opposed first and second electrically conductive layers, positioned on either side of spacer layer 42, 142, 242 can define the top and bottom walls of reaction cell 24, 124, 224. The area of first electrically conductive layer 40, 140, 240 exposed within reaction cell 24, 124, 224 can define the first electrode 26, 126, 226 and the area of the second electrically conductive layer 44, 144, 244 exposed within reaction cell 24, 124, 224 can define second electrode 28, 128, 228. In one aspect, the first and second electrodes are in a non-planer configuration, and preferably, are in an opposed configuration.

A reagent layer can be disposed within reaction cell 24, 124, 224 using a process such as, for example, slot coating, coating by dispensing liquid from the end of a tube, ink jetting, and screen printing. Such processes are described, for example, in the following U.S. Pat. Nos. 6,749,887; 6,689,411; 6,676,995; and 6,830,934, which are hereby incorporated by reference in their entirety. In one embodiment, reagent layer 72, 172, 272 is deposited onto the first electrode and includes at least a mediator and/or an enzyme. A mediator can be in either of two redox states which can be referred to as an oxidizable substance or a reducible substance. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on a pyrroloquinoline quinone co-factor, and GDH based on a nicotinamide adenine dinucleotide co-factor. One exemplary reagent formulation, which would be suitable for making reagent layer is described in pending U.S. application Ser. No. 10/242,951 which is hereby incorporated by reference in its entirety.

As mentioned above, exemplary layers of cells 10, 110, and 210 are individually illustrated in FIGS. 7A through 9D. In one aspect, the electrically conductive layers include an electrically conductive material on one surface and an insulating material on the opposite surface. For example, first electrically conductive layer 40, 140, 240 can include an electrically conductive material on a bottom surface and an insulating material on a top surface, while the second electrically conductive layer 44, 144, 244 can include an electrically conductive material on a top surface and an insulating material on a bottom surface. When the layers are combined into a laminate, the electrically conductive material on the bottom surface faces the electrically conductive material on the top surface.

The first and second electrically conductive layers can be shaped such that when combined, the sensor includes laterally spaced electrical contact areas. With respect to the layers of sensor 10, shown in FIGS. 7A through 7C, the first and second electrically conductive layers can include extension portions 60, 62. When combined, the extension portion 62 of the first electrically conductive layer 40 can extend beyond the spacer layer 42 and the second electrically conductive layer 44 to form second electrical contact area 30. Similarly, extension portion 60 of the second electrically conductive layer 44 can extend beyond the spacer layer 42 and the first electrically conductive layer 40 to form first electrical contact area 32. The first and second electrically conductive layers 140, 144, 240, 244 of sensors 110, 210 can similarly include extension portions 160, 162, 260, 262 that provide electrical contact areas 130, 132, 230, 232.

Spacer layer 42 of sensor 10, as illustrated in FIG. 5B, can include longitudinal aperture 66 that will form electrochemical reaction cell 24 when the layers are combined. In one embodiment, length $L_1$ of aperture 66 (e.g., along the longitudinal axis) is equal to the to the length $L_1$ of first and second electrically conductive layers 40, 44, such that the proximal end of aperture 66 forms sample ingress port 46 and the distal end of aperture 66 forms the second opening 48. In an alternative embodiment, the length of aperture 66 could extend less than the full length of spacer layer 42 (not shown) to provide a reaction cell 24 that extends less than the full width of sensor 10. Sensors 110, 210 can similarly include apertures 166, 266 that define electrochemical reaction cells 124, 244.

Figure 8A:
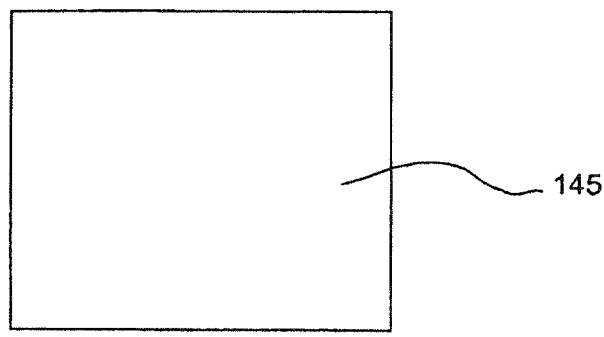
FIG. 8A is a top view of the sealing layer of the of the sensor of FIG. 4A
Figure 8B:
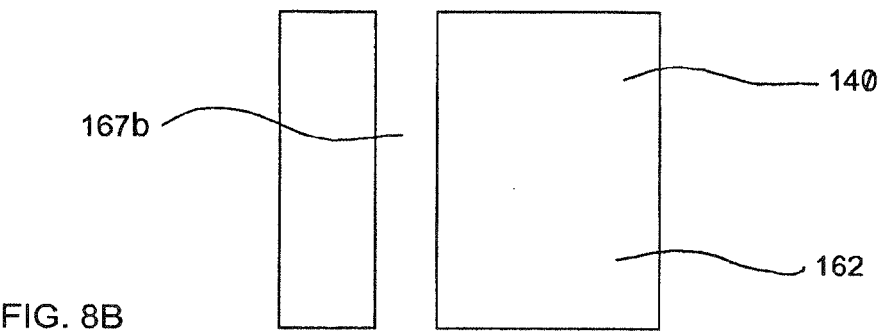
FIG. 8B is a top view of a first electrically conductive layer of the sensor of FIG. 4A.
Figure 8C:
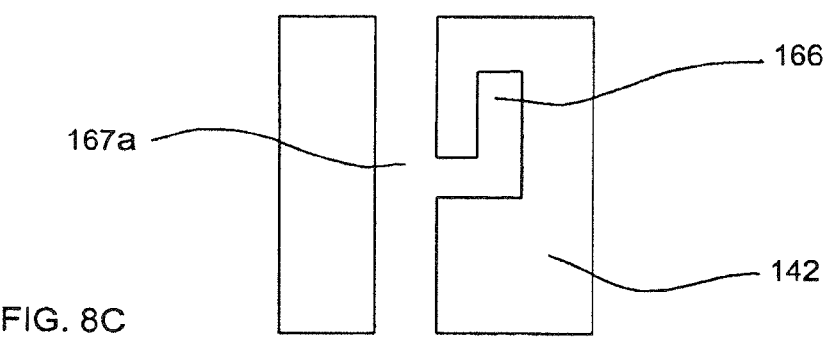
FIG. 8C is a top view of a spacer layer of the sensor of FIG. 4A.
Figure 8D:
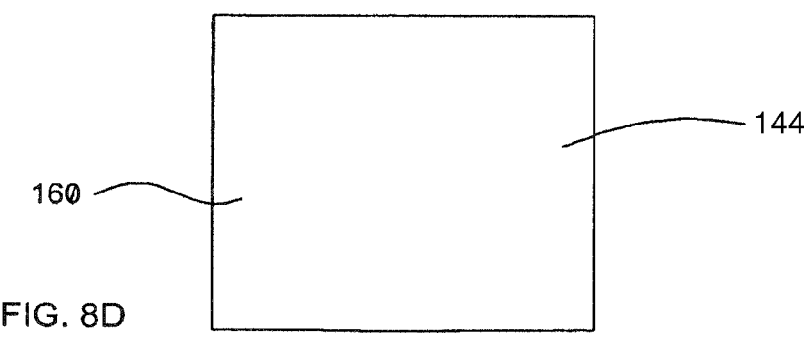
FIG. 8D is a top view of a second electrically conductive layer of the sensor of FIG. 4A.
Figure 9A:
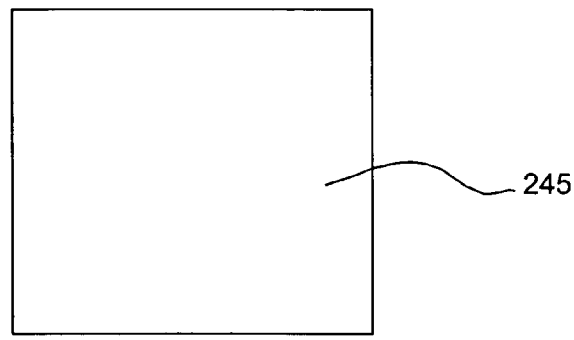
FIG. 9A is a top view of the sealing layer of the of the sensor of FIG. 6A.
Figure 9B:
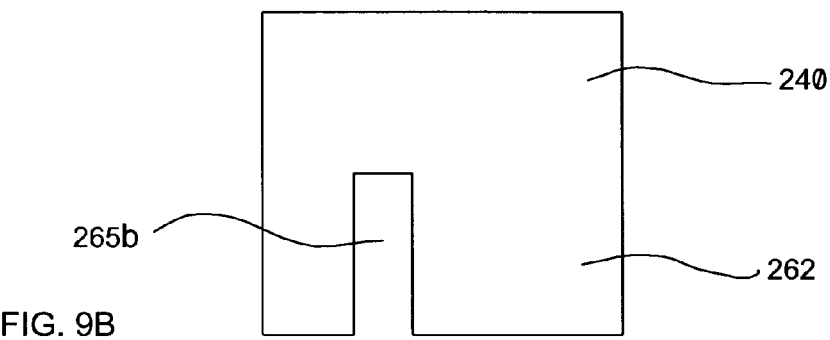
FIG. 9B is a top view of a first electrically conductive layer of the sensor of FIG. 6A.
Figure 9C:
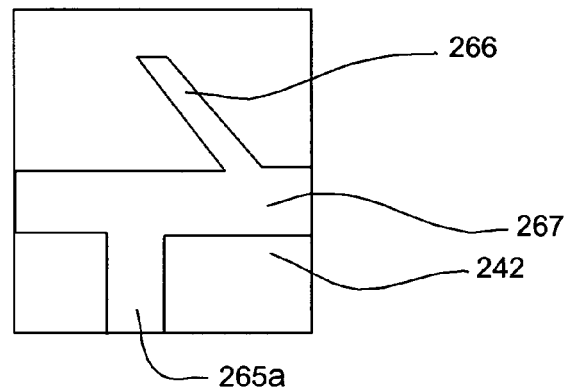
FIG. 9C is a top view of a spacer layer of the sensor of FIG. 6A.
Figure 9D:
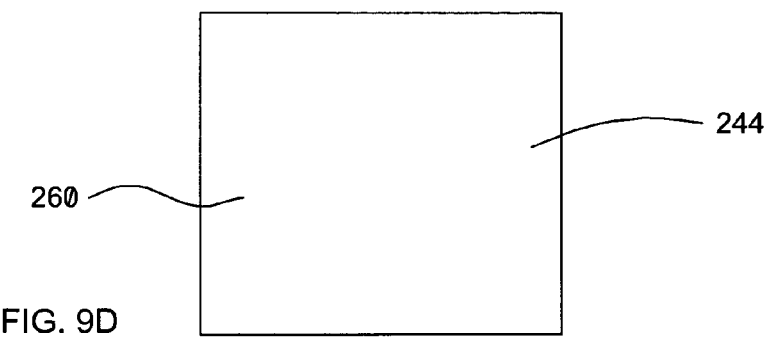
FIG. 9D is a top view of a second electrically conductive layer of the sensor of FIG. 6A.

With respect to sensor 110, as shown in FIG. 8A though 8D, an additional aperture 167a in the spacer layer can define cell 125. Cell 125 of sensor 110 can have a greater height than cell 124, and the larger dimensions of cell 125 can be created by removing a portion of at least one of first and second electrically conductive layers 140, 144 and illustrated as aperture 167b. FIGS. 8B and 8C illustrate an apertures 167a, 167b, in spacer layer 142 and first electrically conductive layer 140, that can define cell 125.

To enclose cell 125 of sensor 110, a sealing layer 145 can be positioned over aperture 167b. Sealing layer 145 can be formed from of a variety of materials, such as for example, the materials used to form the spacer layer. Sealing layer 145 can also provide a cover for a pre-formed vent hole 135. To open vent 135, sealing layer 145 can be punctured.

With respect to sensor 210, cells 225, 224 can be formed by apertures in spacer layer 242 as shown in FIG. 9C. For example, apertures 266, 267 in spacer layer 242 can define cells 225, 224. A third aperture 265a in spacer layer 242 can define cell 221. Cell 221 can have a greater height than cells 225, 224. The larger dimensions of cell 221 can be created by removing a portion of at least one of first and second electrically conductive layers 240, 244. In the first electrically conductive layer 240 illustrated in FIG. 9B, an aperture 265b defines a portion of cell 221.

To enclose cell 221 of sensor 210, a sealing layer 245 (FIG. 9A) can be positioned over apertures 265a, 265b. Sealing layer 245 can be form of a variety of materials, such as for example, the materials used to form the spacer layer. Sealing layer 245 can also provide a cover for a pre-formed vent hole 235. To open vent 235, sealing layer 245 can be punctured.

As discussed above, the sensors disclosed herein can include connective flaps that connect two or more adjacent sensor. Spacer layer 42, 142, 242 of cells 10, 110, 210 can provide the connection between adjacent sensors, and in one embodiment, the spacer layer is shaped such that when the layers of sensor 10, 110, 210 are brought together, an area of the spacer layer extends beyond the first and second electrically conductive layers. For example, connective flaps 34 (FIG. 1A) can be formed by a portion (or portions) of spacer layer 42 extending beyond the first and second electrically conductive layers. The connective flaps 34 can join with connective flaps on an adjacent sensor to provide a connection between sensors. When the connective flaps of adjacent sensor are joined, the connected sensors form an array of two or more sensors. As shown in FIG. 1A, sensor 10 can include a pair of proximal flaps 34 and a pair of distal flaps 34. The proximal set of connective flaps can be connected to a set of distal connective flaps on an proximally positioned adjacent sensor and the distal set of connective flaps can be connected to a set of proximal connective flaps on a distally positioned adjacent sensor. While a set of two connective flaps are shown in the FIGS., in an alternative embodiment, more flaps (e.g., three or more) or fewer flaps (one) could form the connection between adjacent sensors in an array of sensors. One skilled in the art will appreciate that sensors 110, 210 could include similar flaps for joining adjacent sensors (not illustrated).

In one aspect, the connective flaps allow adjacent sensors to move relative to one another by creating a pivot point (e.g., hinge) such that adjacent sensors can pivot with respect to one another. In order to provide relative movement between sensors, the spacer layer can be formed from a flexible or bendable material. For example, the flaps (and spacer layer) can be formed from a polymeric material such as a polyester film. One such material is Melinex® PET polyester film from Dupont, Inc. One skilled in the art will appreciate that the spacer material and spacer layer thickness can be chosen to control the amount of flap flexibility.

In an alternative embodiment, the flaps are defined by a portion of a different layer. For example, the electrically conductive layers and/or the sealing layer (145, 245) could include a portion that defines a connective flap.

The connective flaps preferably have enough strength to hold a series of sensors together, but can be broken or torn to allow individual sensors to be dispensed. One skilled in the art will appreciate that the cross sectional area of the flaps (i.e., thickness and/or width) and/or flap material can be adjusted to provide the desired flap strength. In addition, the flaps can be notched or perforated to facilitate tearing.

Figure 10B:
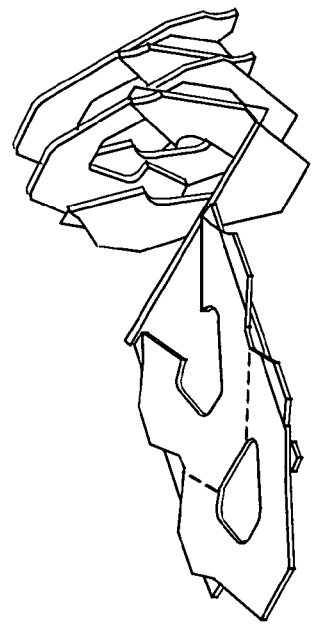
FIG. 10B is a perspective view of an array of connected sensors positioned for delivery in a reaction cell first orientation.
Figure 10A:
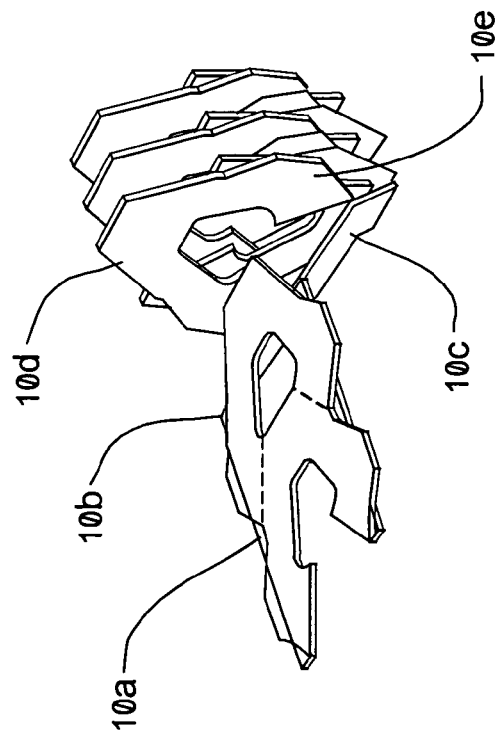
FIG. 10A is a perspective view of an array of connected sensors.

FIGS. 10A and 10B illustrate an array or a series of connected sensors which are mated to one another via connective flaps. Sensors 10a and 10b can be positioned in a coplanar configuration and then pivoted into a folded configuration as shown between sensors 10c, 10d, and 10e. The folded configuration allows the sensors to be stored using a minimal amount of space. When needed, the sensors can then be unfolded and individually dispensed. While flaps 34 are illustrated with respect to sensor 10, one skilled in the art will appreciate that sensors 110, 210 could include similar features.

In use, an array of sensors can be dispensed from a stand alone sensor dispenser or positioned within a meter. Sensor dispensers that can be used with the sensor 10, 110, 210 are disclosed, for example, in a U.S. Application entitled "Sensor Dispenser Device and Method of Use," filed contemporaneously, and hereby incorporated by reference in its entirety.

Figure 11A:
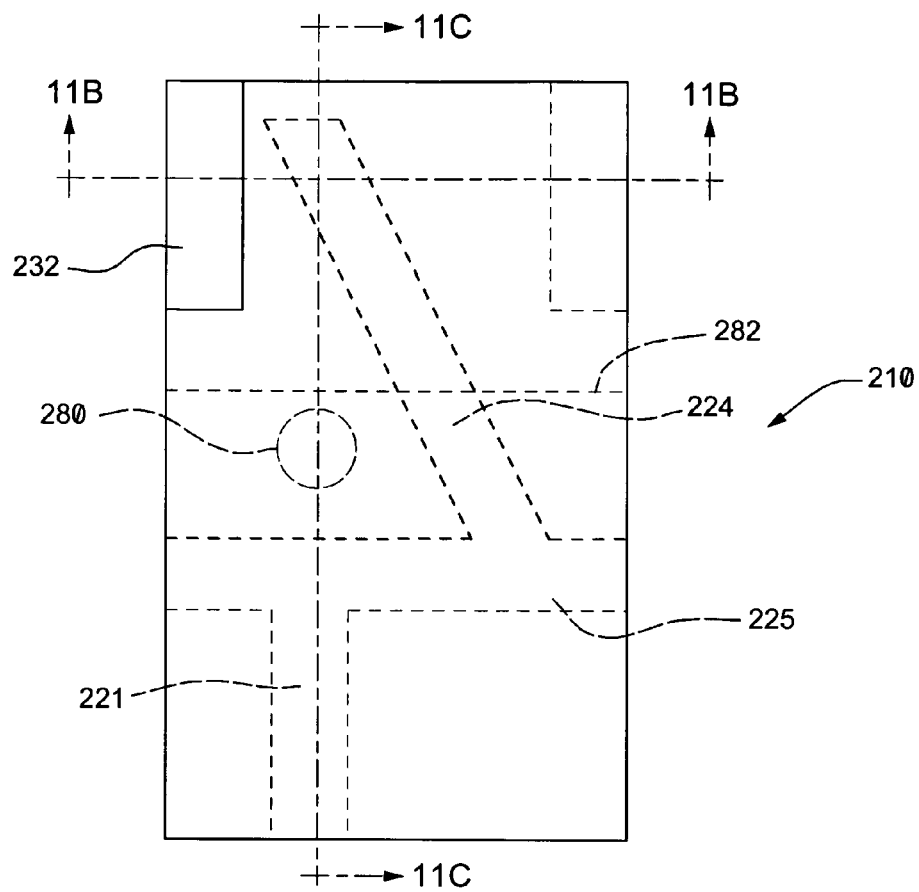
FIG. 11A is a top view of an embodiment of the sensor described herein having three electrical contact areas.
Figure 11B:
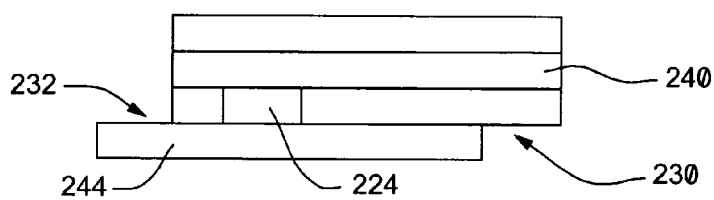
FIG. 11B is a cross sectional view of the sensor of FIG. 11A along the line B-B.
Figure 11C:
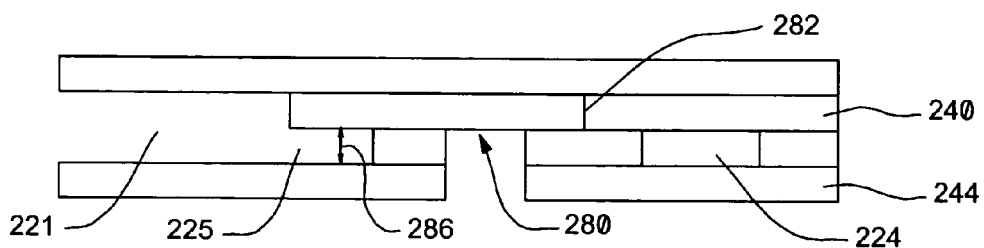
FIG. 11C is a cross sectional view of the sensor of FIG. 11A along the line C-C.

In another embodiment disclosed herein, a third electrical contact area is provided for sensing the status of the prechamber and/or immunological chamber. FIG. 11A through 11C illustrate an embodiment of sensor 210 with third electrical contact area 280. When cells 221 and 225 are filled with a sample, a "filled" condition can be sensed with an electrical connection between third electrical contact area 280 on the first electrically conductive layer 240 and the second electrical contact area 232 on the second electrically conductive layer 244. For example, as shown in FIG. 11C, when sample fills cell 225, the sample bridges the gap between areas the opposed electrically conductive layers 240, 244 and provide an electrical connection between first and second electrically conductive layers. The electrical connection between the first and second electrically conductive layers is illustrated as 286 in FIG. 11C. This electrical connection can be detected by contacting third electrical contact area 280 and second electrical contact area 232. Based on the detection of a closed circuit, a user can determine if/when cell 225 has been properly filled. Once a filled condition is detected, the residence time of the sample within cell 225 can be monitored. After a pre-determined amount of time has elapsed, vent 235 in cell 224 can be opened to allow sample to flow into the electrochemical reaction chamber.

Once a portion of the sample moves into cell 224, first and second electrical contact areas 230, 232 can be used to monitor an electrochemical reaction. In order to differentiate between electrical currents in cells 225 and 224, a break in the electrically conductive path between third electrical contact area 280 and first electrical contact area 230 can be formed in sensor 210. As shown in FIGS. 11A and 11C, an electrical break 288 can be positioned between the electrical contact areas 280 and 230 in the first electrically conductive layer.

One skilled in the art will appreciate further features and advantages of the invention based on the above-described embodiments. Accordingly, the invention is not to be limited by what has been particularly shown and described, except as indicated by the appended claims. In addition, one skilled in the art will appreciate that embodiments described with respect to only one or two of sensors 10, 110, 210 can be implemented in the other sensors. All publications and references cited herein are expressly incorporated herein by reference in their entirety.

What is claimed is:

1. An electrochemical device, comprising:
a first electrically conductive layer including a first electrode area and an opposing second electrically conductive layer including a second electrode area, wherein at least one of the first or second electrically conductive layers comprises an electrically conductive material and an insulating material, wherein the electrically conductive material is coextensive with the insulating material;
a spacing layer positioned between the first and second electrically conductive layers and a sealing layer positioned adjacent to one of the first and second electrically conductive layers;
an electrochemical cell defined by the first and second electrically conductive layers, and an opening in the spacing layer;
an immunological cell defined by one of the first and second electrically conductive layers, the sealing layer, and an opening in the spacing layer and at least one of the first and second electrically conductive layers;
first and second electrical contact areas spaced laterally from the electrochemical cell; and
a sample passageway between the electrochemical cell and the immunological cell, wherein a sample can flow from the immunological cell to at least a portion of the electrochemical cell through the sample passageway.

2. The device of claim 1, wherein the electrochemical cell extends longitudinally.

3. The device of claim 1, wherein the first and second electrical contact areas are positioned on opposite lateral sides of the electrochemical cell.

4. The device of claim 1, wherein the immunological cell extends from a proximal sidewall of the device to a distal sidewall of the device.

5. The device of claim 1, wherein one of the first and second electrically conductive layers includes a vent hole that defines a portion of a vent.

6. The device of claim 5, wherein the vent hole is covered by the sealing layer.

7. The device of claim 1, further comprising a sample ingress opening through which the sample can be delivered to the immunological cell.

8. The device of claim 1, wherein the electrochemical cell is adapted to draw sample into the electrochemical cell through the sample passageway via capillary action.

9. The device of claim 1, wherein the electrochemical cell and the immunological cell extend parallel to a central longitudinal axis of the device.

10. The device of claim 1, wherein the electrochemical cell and the immunological cell extend along a central longitudinal axis of the device.

11. The device of claim 1, wherein the first electrical contact area is positioned adjacent to a first lateral edge of the device and the second electrical contact area is positioned adjacent to a second lateral edge of the device.

12. The device of claim 1, wherein the first electrical contact area is positioned on a top surface of the device and the second electrical contact area is positioned on a bottom surface of the device.

13. The device of claim 1, wherein a connective flap extends beyond the first and second electrically conductive layers for connecting with another electrochemical sensor device.

14. The sensors of claim 13, wherein the connective flap is defined by a layer selected from the group consisting of the spacer layer, the sealing layer, and combinations thereof.

15. The sensor of claim 1, further comprising a third electrical contact area.

16. The sensor of claim 15, wherein an electrical circuit between the third electrical contact area and at least one of the first and second electrical contact areas is closed when the immunological cell is filled with sample.

17. An electrochemical device, comprising:
a first electrically conductive layer including a first electrode area and an opposing second electrically conductive layer including a second electrode area, wherein at least one of the first or second electrically conductive layers comprises an electrically conductive material and an insulating material, wherein the electrically conductive material is coextensive with the insulating material;
a spacing layer positioned between the first and second electrically conductive layers and a sealing layer positioned adjacent to one of the first and second electrically conductive layers;
an electrochemical cell defined by the first and second electrically conductive layers, and an opening in the spacing layer;
an immunological cell defined by the first and second electrically conductive layers, and an opening in the spacing layer;
a pre-chamber defined by one of the first and second electrically conductive layers, the sealing layer, and an opening in at least one of the spacing layer and at least one of the first and second electrically conductive layers;
first and second electrical contact areas spaced laterally from the electrochemical cell; and
a sample passageway between the electrochemical cell and the immunological cell, wherein a sample flows from the immunological cell to at least a portion of the electrochemical cell through the sample passageway.

18. An electrochemical device, comprising:
a first electrically conductive layer including a first electrode area and an opposing second electrically conductive layer including a second electrode area, wherein at least one of the first or second electrically conductive layers comprises an electrically conductive material and an insulating material, wherein the electrically conductive material is coextensive with the insulating material;
a spacing layer positioned between the first and second electrically conductive layers and a sealing layer positioned adjacent to one of the first and second electrically conductive layers;
a first cell defined by the first and second electrically conductive layers, and an opening in the spacing layer;
first and third electrical contact areas in electrical communication with the first electrically conductive layer and a second electrical contact area in electrical communication with the second electrically conductive layer;
a second cell defined by one of the first and second electrically conductive layers, the sealing layer, and an opening in the spacing layer and at least one of the first and second electrically conductive layers; and
a sample passageway between the first cell and the second cell, wherein a sample flows from the second cell to at least a portion of the first cell through the sample passageway.

19. The sensor of claim 18, wherein the first and second electrical contact areas are spaced laterally from the at least one cell.

* * * * *